(12) United States Patent
Cowan et al.

(10) Patent No.: US 11,401,079 B2
(45) Date of Patent: Aug. 2, 2022

(54) TAMPER EVIDENT CAP

(71) Applicant: GBUK Group Limited, Selby (GB)

(72) Inventors: Joseph Cowan, Selby (GB); Ross Allsopp, Selby (GB); Nicholas Scard, Selby (GB)

(73) Assignee: GBUK Group Limited, Selby (GB)

( * ) Notice: Subject to any disclaimer, the term of this patent is extended or adjusted under 35 U.S.C. 154(b) by 0 days.

(21) Appl. No.: 17/146,079

(22) Filed: Jan. 11, 2021

(65) Prior Publication Data

US 2021/0214130 A1 Jul. 15, 2021

(51) Int. Cl.
   *B65D 41/34* (2006.01)

(52) U.S. Cl.
   CPC ...... *B65D 41/3423* (2013.01); *B65D 2401/15* (2020.05)

(58) Field of Classification Search
   CPC .......... B65D 41/3423; B65D 2401/15
   USPC ............. 220/266; 215/252, 250, 330, 331
   See application file for complete search history.

(56) References Cited

U.S. PATENT DOCUMENTS

| 4,190,169 A | | 2/1980 | Pehr | |
| 4,401,227 A | * | 8/1983 | Pehr | B65D 41/3447 215/252 |
| 4,553,678 A | | 11/1985 | Thorsbakken | |
| RE32,879 E | * | 2/1989 | Wright | B65D 41/3428 215/252 |
| 4,930,647 A | * | 6/1990 | Dutt | B65D 41/3409 215/252 |
| 4,998,988 A | | 3/1991 | Zinnbauer | |
| 5,115,934 A | * | 5/1992 | Nelson | B29C 45/4407 220/276 |
| 5,957,315 A | | 9/1999 | Kaitsuka | |
| 5,979,681 A | * | 11/1999 | PatrickJean-Luc Andre | B65D 50/046 215/216 |
| 6,039,196 A | * | 3/2000 | Ekkert | B65D 50/04 215/216 |

(Continued)

FOREIGN PATENT DOCUMENTS

| EP | 0052167 A1 | 5/1982 |
| EP | 539894 A1 | 5/1993 |

(Continued)

OTHER PUBLICATIONS

GB Search Report for Application No. GB2000444.6 dated Jun. 30, 2020.

(Continued)

*Primary Examiner* — J. Gregory Pickett
*Assistant Examiner* — Niki M Eloshway
(74) *Attorney, Agent, or Firm* — Harness, Dickey & Pierce, P.L.C.

(57) ABSTRACT

The invention relates to a tamper evident cap for removable screwing onto a fluid outlet provided on an enteral fluid source, the cap includes a tamper evident feature comprising a deflectable element configured to be momentarily deflectable in a longitudinal direction by a deflecting element provided on the fluid outlet as the cap is screwed onto the fluid outlet, and wherein the deflectable element is configured to be permanently deflected outwardly in relation to the longitudinal axis by the deflecting element as the cap is unscrewed from the fluid outlet to provide a visual indication that the cap has been unscrewed.

11 Claims, 17 Drawing Sheets

(56) References Cited

U.S. PATENT DOCUMENTS

| | | | |
|---|---|---|---|
| 6,264,052 B1 | 7/2001 | Schmitz | |
| 6,279,766 B1 * | 8/2001 | Jones | B65D 50/046 215/216 |
| 8,528,758 B2 * | 9/2013 | Morlot | B65D 47/36 215/252 |
| 8,627,968 B2 * | 1/2014 | Baban | B65D 55/022 215/220 |
| 2002/0043142 A1 | 4/2002 | Zumbuhl | |
| 2002/0134747 A1 | 9/2002 | Babcock et al. | |
| 2003/0146183 A1 | 8/2003 | Montgomery | |
| 2004/0007576 A1 | 1/2004 | Morris | |
| 2006/0207960 A1 * | 9/2006 | Bastero Lopez | B65D 55/022 215/331 |
| 2006/0207980 A1 | 9/2006 | Bastero Lopez | |
| 2007/0108154 A1 | 5/2007 | Niwa et al. | |
| 2007/0131641 A1 | 6/2007 | Higgins | |
| 2007/0284398 A1 | 12/2007 | Baughman et al. | |
| 2008/0135513 A1 | 6/2008 | Umenaka | |
| 2009/0308833 A1 | 12/2009 | Andersson et al. | |
| 2010/0187233 A1 | 7/2010 | Fraser et al. | |
| 2010/0213213 A1 | 8/2010 | Albers et al. | |
| 2010/0282705 A1 | 11/2010 | Ledemeney | |
| 2013/0136382 A1 | 5/2013 | Barron | |
| 2013/0299495 A1 | 11/2013 | Last et al. | |
| 2014/0263475 A1 | 9/2014 | Totten | |
| 2015/0166225 A1 | 6/2015 | van Alfen et al. | |
| 2015/0344192 A1 | 12/2015 | Ceccherini | |
| 2016/0242998 A1 | 8/2016 | Brandenburger et al. | |
| 2017/0217646 A1 | 8/2017 | Hanan | |
| 2018/0280234 A1 * | 10/2018 | Brevik-Andersen | A61J 1/1481 |
| 2018/0370698 A1 | 12/2018 | Thomsen | |
| 2019/0009943 A1 | 1/2019 | Komet et al. | |

FOREIGN PATENT DOCUMENTS

| | | |
|---|---|---|
| EP | 0965533 A1 | 12/1999 |
| EP | 1281627 A2 | 2/2003 |
| EP | 2586721 A1 | 5/2013 |
| GB | 2241231 A | 8/1991 |
| GB | 2277320 A | 10/1994 |
| GB | 2563401 A | 12/2018 |
| WO | WO-8300674 A1 | 3/1983 |
| WO | 90/05681 A1 | 5/1990 |
| WO | WO-0048920 A1 | 8/2000 |
| WO | WO-0168469 A1 | 9/2001 |
| WO | WO-2005009854 A1 | 2/2005 |
| WO | WO-2007045747 A1 | 4/2007 |
| WO | WO-2008132665 A1 | 11/2008 |
| WO | WO-2008142413 A1 | 11/2008 |
| WO | WO-2015189436 A1 | 12/2015 |
| WO | WO-2018069153 A1 | 4/2018 |
| WO | WO-2019106369 A1 | 6/2019 |
| WO | 2020/128056 A1 | 6/2020 |

OTHER PUBLICATIONS

Extended European search report for European Patent Application No. 21150420.4, dated Jun. 18, 2021.

Combined Search and Examination Report for Application No. GB2100143.3 dated Jul. 1, 2021.

* cited by examiner

TAMPER EVIDENT CAP

CROSS-REFERENCE TO RELATED APPLICATIONS

This application claims priority to British Patent Application No. GB 2000444.6, filed Jan. 13, 2020. The entire disclosure of the above application is incorporated herein by reference.

FIELD OF THE INVENTION

This invention relates to a tamper evident cap for use on an enteral fluid source, such as an enteral feeding bag.

BACKGROUND OF THE INVENTION

Fluid delivery systems, such as feeding tubes, are used to deliver nutrients and medicine to patients. The state of being fed by a feeding tube is commonly known in the art as enteral feeding. A tube is inserted in the mouth or nasal opening of the patient, via the esophagus, for delivery of the fluid into the gastrointestinal system.

The enteral fluid is often provided in an enteral feeding bag or pouch. Tamper evident or tamperproof caps are conventionally used on enteral feed bags to demonstrate whether the cap has been unscrewed. This is because any unauthorised access of the bag could result in the enteral fluid being compromised, for example by a breach in sterility, or by being spiked with potentially dangerous substances.

An example of a tamper evident cap used on an enteral feeding bag is a screw cap with a breakaway ring. However, it is often difficult to visualise the breakage of the tamper evident feature. There is therefore a need for a tamper evident cap that the user can unambiguously visually ascertain that the cap has been unscrewed.

SUMMARY OF THE INVENTION

According to a first aspect of the invention there is provided a tamper evident cap for removably screwing onto a fluid outlet provided on an enteral fluid source, wherein the cap comprises:
  an elongate main body having a distal end and a proximal end and a longitudinal axis extending therebetween;
  a tamper evident feature comprising a deflectable element configured to be momentarily (e.g. temporarily, reversibly) deflectable in a longitudinal direction by a deflecting element provided on the fluid outlet as the cap is screwed onto the fluid outlet, and wherein the deflectable element is configured to be permanently deflected outwardly in relation to the longitudinal axis by the deflecting element provided on the fluid outlet as the cap is unscrewed from the fluid outlet to provide a visual indication that the cap has been unscrewed.

The deflectable element is momentarily deflectable in a longitudinal direction in that it is configured to be deflected by the deflecting element only whilst the deflecting element is in contact with and applying force in a longitudinal direction to the deflectable element (e.g. as the cap is screwed onto the spout). When the deflecting element is no longer applying force in a longitudinal direction then the deflectable element returns to its non-deflected position.

In some constructions, the tamper evident feature comprises a plurality of deflectable elements spaced apart about the proximal end of the cap. For example, a plurality of deflectable elements may be spaced apart about the proximal end of the cap. In some constructions, a first deflectable element and a second deflectable element are positioned diametrically opposite each other. In some constructions, a first deflectable element and a second deflectable element are positioned radially opposite each other.

The deflectable element may be in the form of a deflectable arm.

In some constructions, the deflectable arm extends circumferentially about a portion of the cap.

In some constructions, a first end of the deflectable arm is permanently connected to the proximal end of the cap. Tis connection provides a hinge about which the arm can be deflected outwardly. This connection may remain intact in both the untampered and tampered states or may be intact in the untampered state and severed or damaged in the tampered state.

In some constructions a second end of the deflectable arm is temporarily connected to the proximal end of the cap via a breakable or snappable connection. This connection may be in the form of a snapping web. The snapping web may be in the form of a snappable finger having a snappable joint. This connection is intact in the untampered state and broken in the tampered state.

In some constructions, the arm slopes upwardly such the second end of the arm is located more proximally than the first end of the arm. An acute angle is defined between the distal or lower surface of the arm and the proximal end of the cap.

In some constructions, the cap further includes an external shell mounted annularly around and spaced apart from the main body of the cap. The external shell may be mounted to the main body of the cap via one or more buttresses. The buttresses may be spaced radially around the main body. The external shell advantageously increases the overall size of the cap, which reduces the risk of the cap posing a choking hazard. The increased size provided by the external shell also makes it easier for a user to grip and unscrew the cap. The external shell also protects the anti-tamper elements from damage during production, sorting and fitting.

The external shell may be provided with one or more gripping features in the form of indentations, protrusions, grooves or other tactile features. The gripping features may be formed integrally with the external shell or may be composed of a different material such as natural or synthetic rubber and attached to the external shell.

In some constructions, the cap is provided with a protective ring positioned annularly around the main body of the cap. The protective ring extends proximally from the proximal end of the cap. The protective ring may be attached directly to the main body. Alternatively where the cap includes an external shell mounted via one or more buttresses, the protective ring may be attached to the buttresses. The protective ring partially surrounds the tamper evident features, helping to protect the tamper evident features from premature damage during production, sorting and assembly. The protective ring also provides a rigid feature to aid in automated orientation and sorting of the caps during the assembly process.

Preferably the protective ring has at least one opening positioned adjacent to, aligned with and of a similar size and shape to the tamper evident feature. This allows a user to easily see the tamper evident feature when the cap is in position on the spout. The opening also enables the tamper evident feature to deflect outwardly from an untampered state to a tampered state when the cap is twisted during removal. A user can clearly see through the opening whether the tamper evident feature is in an untampered or tampered state. Preferably the number and position of openings on the protective ring corresponds to the number and position of tamper evident features on the proximal end of the cap.

In some constructions, the deflecting element on the fluid outlet comprises a projection extending outwardly from a wall of the fluid outlet. The projection is configured to permanently deflect the deflectable arm as the cap is unscrewed from the fluid outlet. The projection may be a cam. The cam may have a substantially C-shape or concave cammed surface.

During unscrewing of the cap, the second end of the deflectable arm is rotated into contact with the cam. As a surface of the arm bears against, and rides along the cammed surface, the arm is forced outwardly. The deflectable arm is then permanently deflected outwardly in relation to the longitudinal axis of the cap which extends between a proximal end and a distal end of the cap. This provides a clear and unambiguous visual indication that the cap has been unscrewed. Where the second end of the deflectable arm is temporarily connected to the proximal end of the cap via a breakable or snappable connection, then the snappable connection is snapped when a sufficient outwardly directed force has been applied to the arm.

In some constructions, the cap may also include a rotational stop feature configured to prevent the cap from being overtightened. When a stop surface on the rotational stop feature is brought into engagement with a radial abutment surface provided on the deflecting element (i.e., the projection) the cap cannot be rotated any further.

The cammed surface and the radial abutment surface may be provided on opposite walls of the projection.

In some constructions, the rotational stop feature may be in the form of a protrusion extending from the proximal end of the cap. The protrusion may be in the form of a fin.

Accordingly, there are two functional interactions between the cap and the deflecting element (i.e., the projection) provided on the fluid outlet. Firstly, the interaction between the deflectable arm on the cap and the cammed surface on the projection which demonstrates unauthorised unscrewing of the cap. Secondly, the interaction between the rotational stop feature on the cap and the radial abutment surface on the projection which prevents overtightening of the cap.

The cap may be provided with grip features to facilitate a user gripping the cap as the cap is screwed onto and unscrewed from the fluid outlet.

According to a second aspect of the invention there is provided a kit comprising a tamper evident cap according to the first aspect of the invention and an enteral fluid source, for example an enteral feeding bag or pouch.

According to a third aspect of the invention there is provided an enteral feeding bag comprising:
 a fluid outlet comprising a connection portion configured to form a connection with an end of an enteral feed tube, and
 a tamper evident cap according the first aspect of the invention removably attached to the fluid outlet.

In some constructions, the fluid outlet comprises a projection extending outwardly from a wall of the fluid outlet. The projection is configured to temporarily deflect the deflectable element in a longitudinal direction as the cap is screwed onto the fluid outlet, and to permanently deflect the deflectable element outwardly with respect to a longitudinal axis when the cap is unscrewed from the fluid outlet. The projection may be a cam. The cam may have a substantially C-shaped or concave cammed surface.

The fluid outlet may be a nozzle or a spout provided on the enteral feeding bag or pouch. Advantageously the nozzle or spout is an integrated ENFit connector is compatible with the requirements of International Standard: ISO 80369-3.

The feeding of a liquid enteral nutritional solution from an enteral fluid source such as from an enteral feeding bag requires a detachable connection to be made between the fluid outlet port of the bag and an end of the enteral feeding tube. Tubing misconnection errors are a potentially deadly problem in healthcare facilities. One type of misconnection error involves incorrectly connecting enteral feeding tubes and intravenous catheters to the wrong fluid sources. Whilst enteral feeding tubes, such as nasogastric feeding tubes, are used to administer liquid nutritional solutions and medications into a patient's gastrointestinal system, intravenous catheters are used to administer liquid nutritional solutions and medications directly into a patient's vascular system. Serious injury, and even death, can occur when substances designed for enteral administration are administered intravenously.

The widespread use of luer connectors for medical tubing, catheters and syringes has contributed to the risk of error as they enable functionally dissimilar delivery tubes to be connected. This has led to the establishment of International Standard: ISO 80369-3 for small bore connectors for liquids and gases. The design requirements make it difficult, if not impossible, for unrelated delivery systems to be connected. ISO 80369-3 connectors for enteral devices are commonly referred to as ENFit connectors and provide a detachable connection via a pair of mating connectors referred to as male and female threaded ENFit connectors.

Currently if enteral fluid is to be delivered from an enteral feeding bag, an adapter or syringe that is configured to cooperate with the ENFit connection at the end of the enteral feeding tube is needed. One reason for this is the requirement that the feed is stored in a tamper evident container. It has proven difficult to integrate a tamper evident feature with an ENFit lure/thread. This has been solved in the present application which enables a tamper evident cap to be used on enteral feeding bag with an ENFit connection. Once the cap has been removed, the enteral feeding bag can be directly connected to an enteral feeding tube.

Accordingly, in some constructions of the second aspect of the invention, the connection portion on the fluid outlet of the enteral feeding bag is an ENFit connector. For example, the connection portion may be a female ENFit connector which is configured to mate with a corresponding male ENFit connector provided at an end of an enteral feeding tube. In other constructions, the connection portion is a male ENFit connector which is configured to mate with a corresponding female ENFit connector provided at an end of an enteral feeding tube.

In the constructions in which the connection portion provided on the fluid outlet is a female ENFit connector, a corresponding male ENFit connector may be provided on the removable cap. In the other constructions in which the connection portion provided on the fluid outlet is a male ENFit connector, a corresponding female ENFit connector may be provided on the removable cap.

BRIEF DESCRIPTION OF THE DRAWINGS

The invention will now be described, by way of example only, with reference to the following drawings, in which.

DETAILED DESCRIPTION OF THE DRAWINGS

Figure 1:
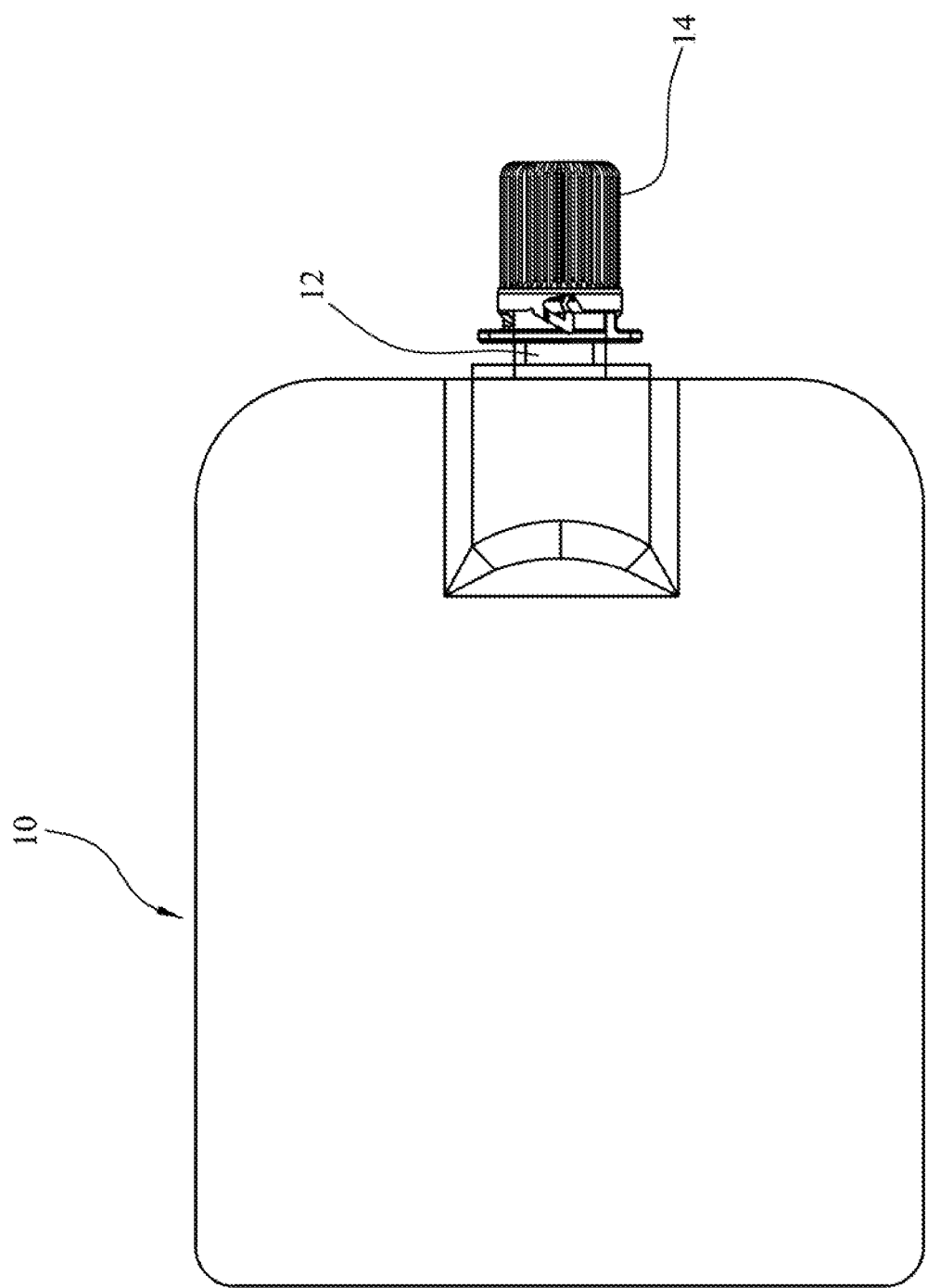
FIG. 1: Illustrates a schematic of an enteral feeding bag having an integrated ENFit connector in combination with a tamper evident cap according to a first embodiment.

With reference to FIG. 1, there is shown an enteral feeding bag 10 according to a first embodiment that includes an integrated female ENFit connector in the form of a spout 12. The spout 12 can be directly connected to a male ENFit connector on the end of an enteral feeding tube without the need for an adapter. A tamper evident cap 14 is screwed onto the spout, and locked in position.

Figure 2:
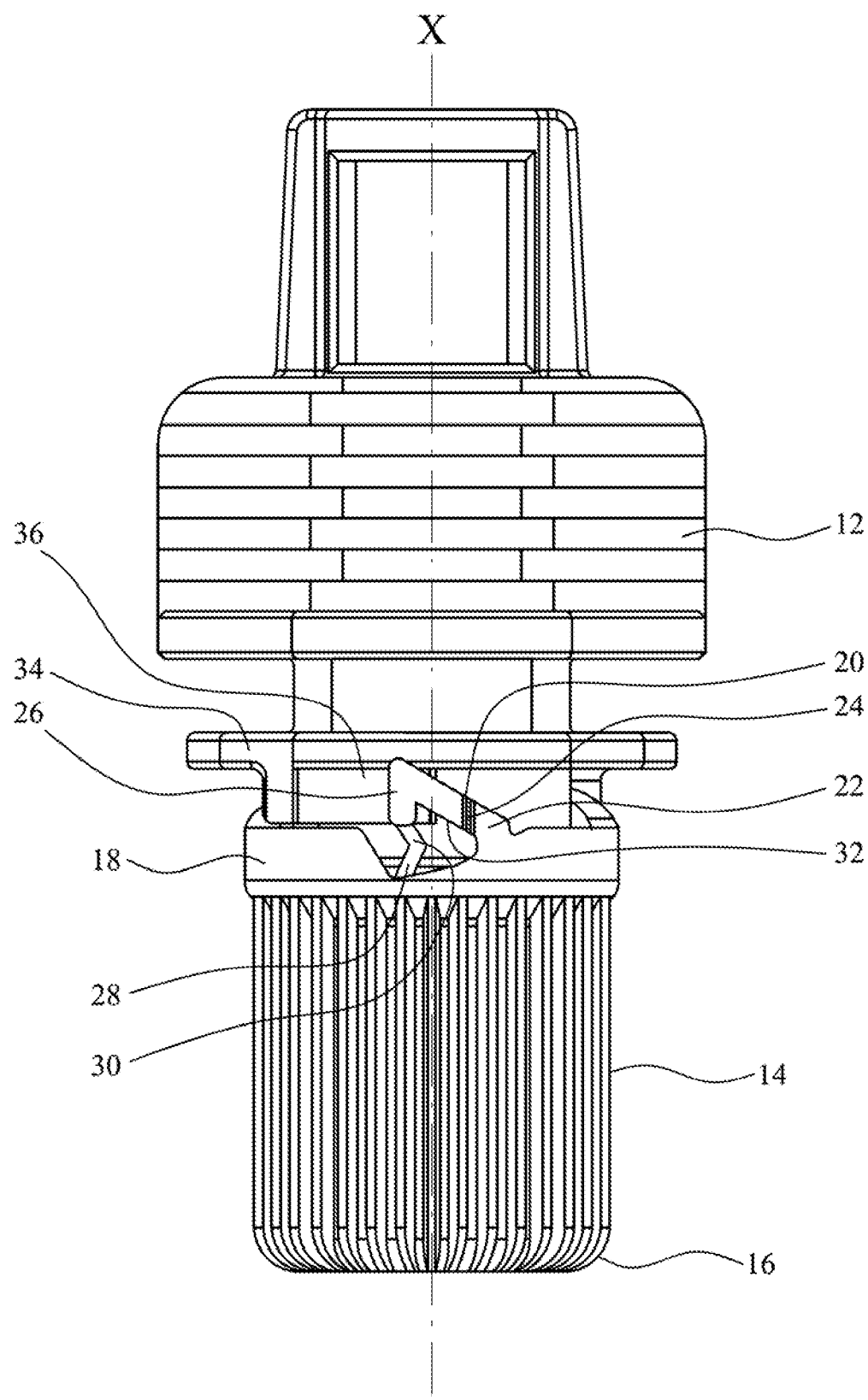
FIG. 2: Is a first front view of the integrated ENFit connector and tamper evident cap of FIG. 1 with the tamper evident cap screwed onto the connector.

FIG. 2 provides a first front view of the tamper evident cap of FIG. 1. The cap has a distal end 16 (i.e. base) and a proximal end 18 (i.e. a rim), and a longitudinal axis (X) extending therebetween.

The cap includes a male ENFit connector in the form of screw threads provided on the interior surface of the cap. The threads form a threaded connection with the complementary screw threads (not shown) of the female ENFit connector arranged on the spout 12.

The proximal end 18 of the cap also includes a tamper evident feature in the form of a deflectable arm 20. Whilst only one deflectable arm is visible in FIG. 2, this construction of the tamper evident cap includes a pair of radially opposed deflectable arms 20. However, it is envisaged that in alternative constructions of the cap, a single deflectable arm may be provided, or more than two deflectable arms may be provided.

As shown, the deflectable 20 arm extends circumferentially about a portion of the cap. A first end 22 is permanently connected to the proximal end 18 of the cap. This connection provides a hinge 24 about which the arm can deflect outwardly. This connection remains intact in both the untampered and tampered states. A second end 26 of the deflectable arm is temporarily connected to the proximal end 18 of the cap via a breakable or snappable connection. As shown in this exemplary construction, this connection may be in the form of a snappable finger 28 having a snappable joint 30. This connection is intact in the untampered state and broken in the tampered state.

Figure 6:
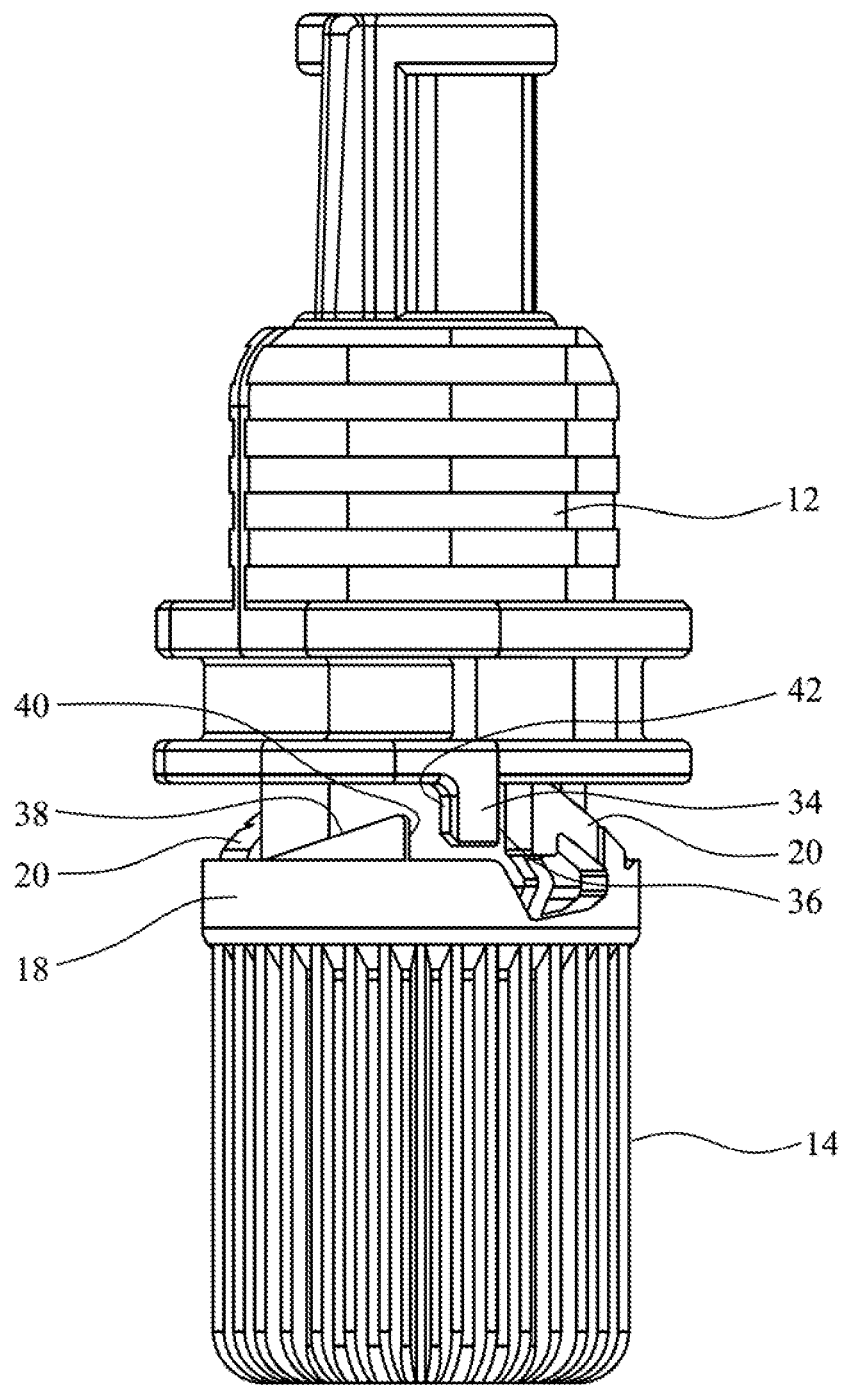
FIG. 6: Illustrates a fourth front view with the tamper evident cap of FIG. 1 screwed onto the connector.

As shown in this exemplary construction, the deflectable arm 20 slopes upwardly such the second end 26 of the arm is located more proximally than the first end 22 of the arm. An acute angle is defined between the distal or lower surface of the arm 32 and the proximal end of the cap. The second end 26 of the arm 20 can therefore temporarily deflect longitudinally (i.e. "nod downwards") as the cap is screwed onto the spout. As best illustrated in FIG. 6, a cutaway portion is provided at the proximal end 18 of the cap 14 to allow the deflectable arm 20 to deflect longitudinally as the cap 14 is screwed onto the spout 12.

Figure 3:
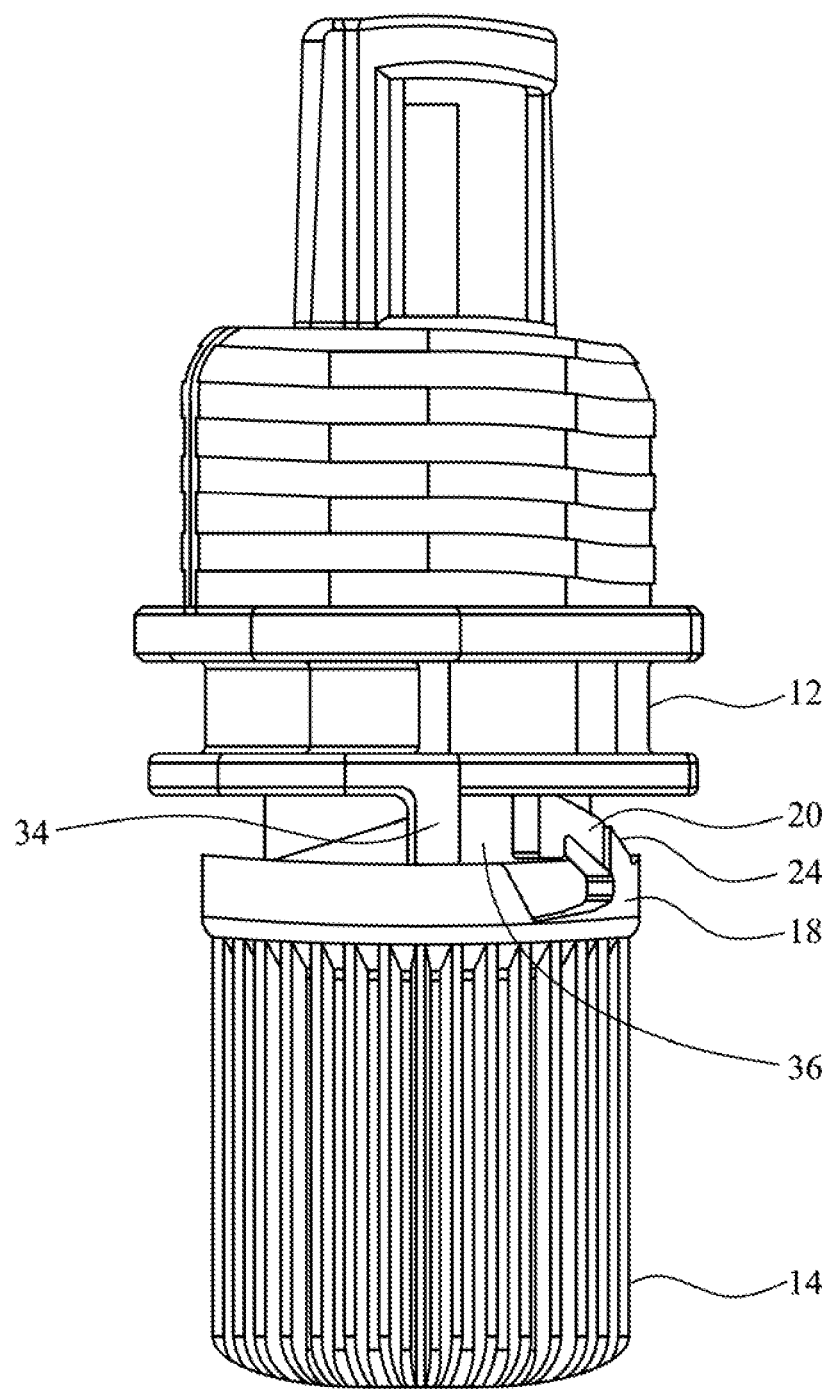
FIG. 3: Is a second front view of the integrated ENFit connector and tamper evident cap of FIG. 1 with the tamper evident cap screwed onto the connector.
Figure 4:
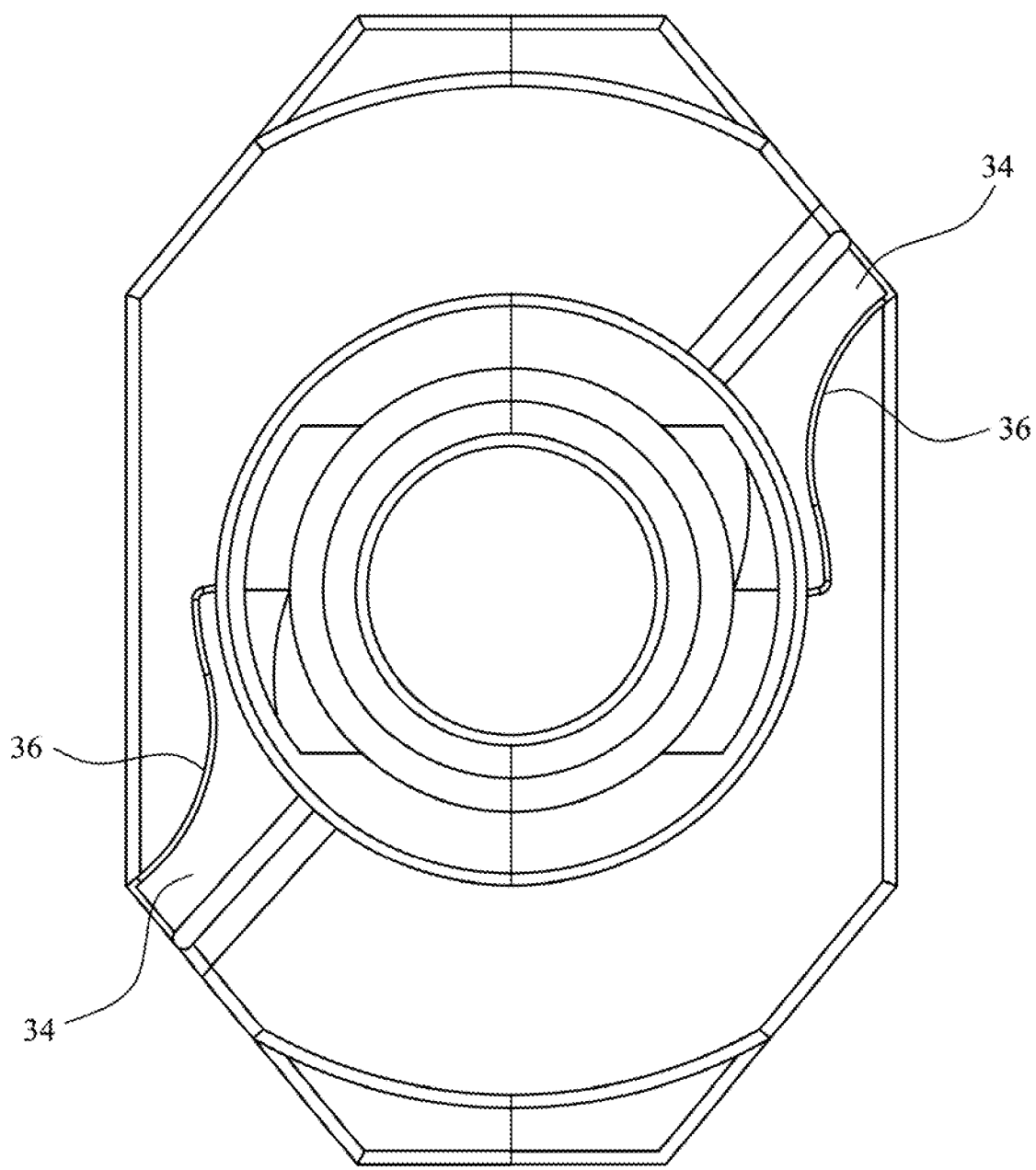
FIG. 4: Is a plan view of the cammed surfaces provided on the integrated ENFit connector of FIG. 1.

Referring now to FIG. 3, the spout 12 includes a deflecting element, shown here in the form of a projection 34, configured to cause the permanent deflection of the deflectable arm when the cap is unscrewed. Whilst only one projection 34 is visible in FIG. 3, as shown in the plan view of the spout 12 (see FIG. 4) this construction of the tamper evident cap includes a pair of radially opposed projections 34. Each projection is configured to interact with one of the pair of deflectable arms. As shown in FIG. 4, the projection is a cam having a substantially concave or C-shaped cammed surface 36.

The cammed surface may have different shapes, for example the cammed surface may slope outwards on a helix.

Figure 5:
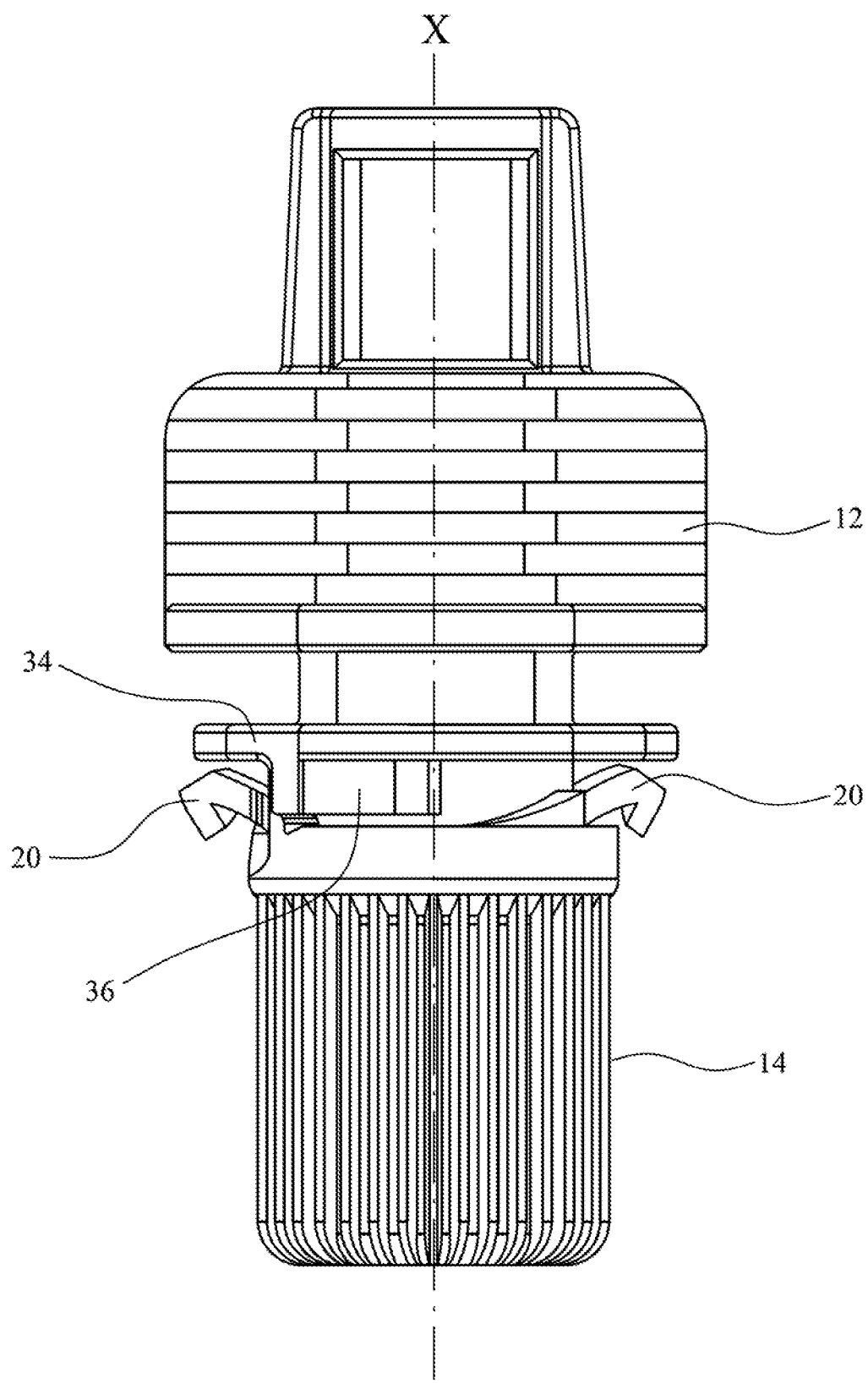
FIG. 5: Is a third front view of the integrated ENFit connector and cap of FIG. 1 showing the cap having been partially unscrewed.

In use, when the tamper evident cap is unscrewed from the spout, either by an authorised or unauthorised user, the second end 26 of each deflectable arm 20 is rotated into contact with the cammed surface 36 of cam 34. As the inner surface of each arm bears against, and rides along the cammed surface 36, the arm is urged outwardly in relation to the longitudinal axis of the cap. The permanent outward deflection of the deflectable arm 20 as the cap is unscrewed is therefore in a different (e.g. substantially perpendicular) plane to the temporary longitudinal deflection as the cap is screwed on to the spout. When a sufficient outwardly directed force has been applied to each arm, the snappable joint 30 of the snappable finger 28 is snapped. The deflectable arm is then permanently deflected, as shown in FIG. 5. Whilst the cap can be re-screwed onto the spout, the permanently deflected arms provide a clear and unambiguous visual indication that the cap has previously been unscrewed.

The discussion above with reference to FIGS. 1 to 6 has focused on the functional interaction of the tamper evident feature (i.e., the deflectable arm 20) provident on the cap with a deflecting element (i.e. the cam 34) provided on the spout. This shows whether the cap has been unscrewed.

Figure 7A:
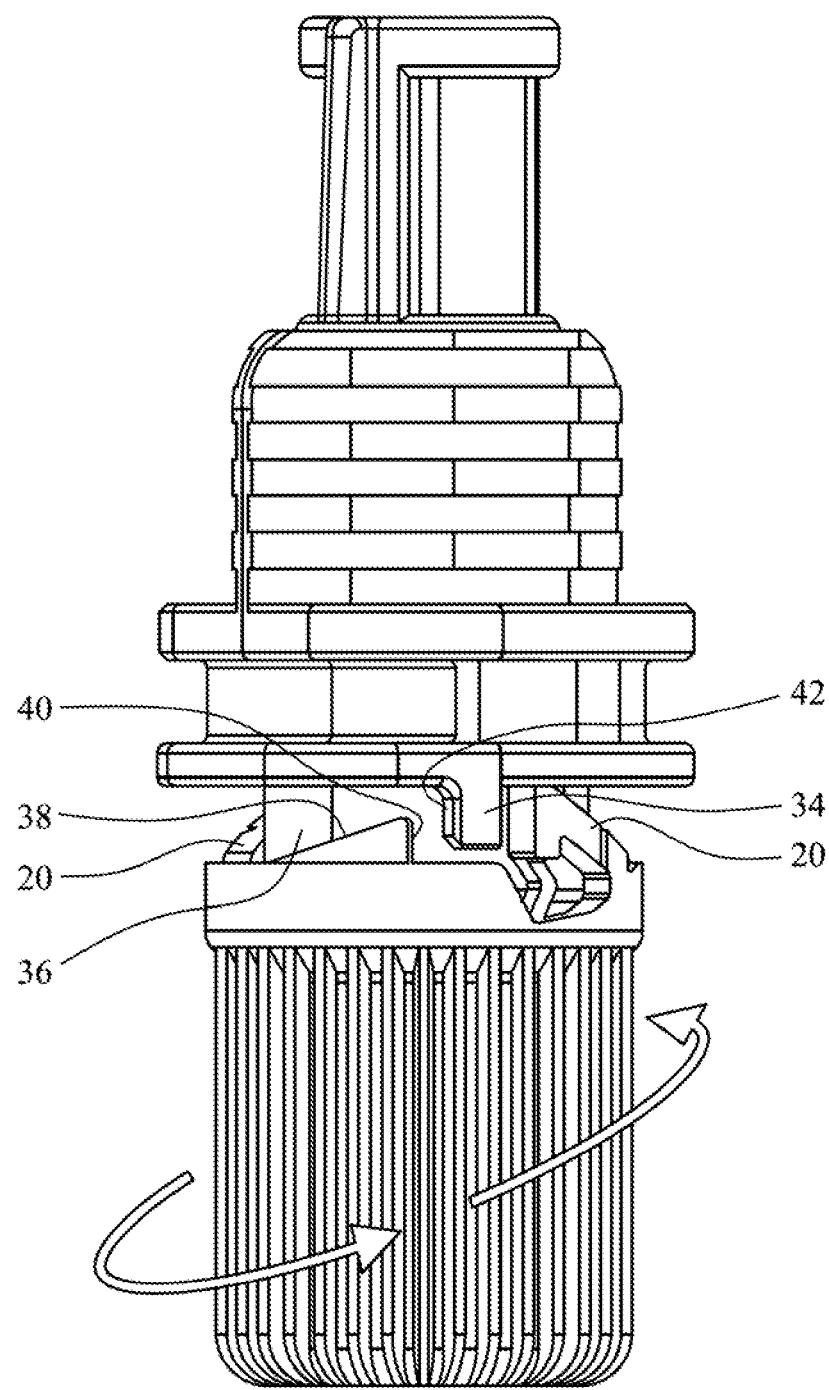
FIG. 7A: Illustrates a process of screwing the cap of FIG. 1 onto the connector.
Figure 7B:
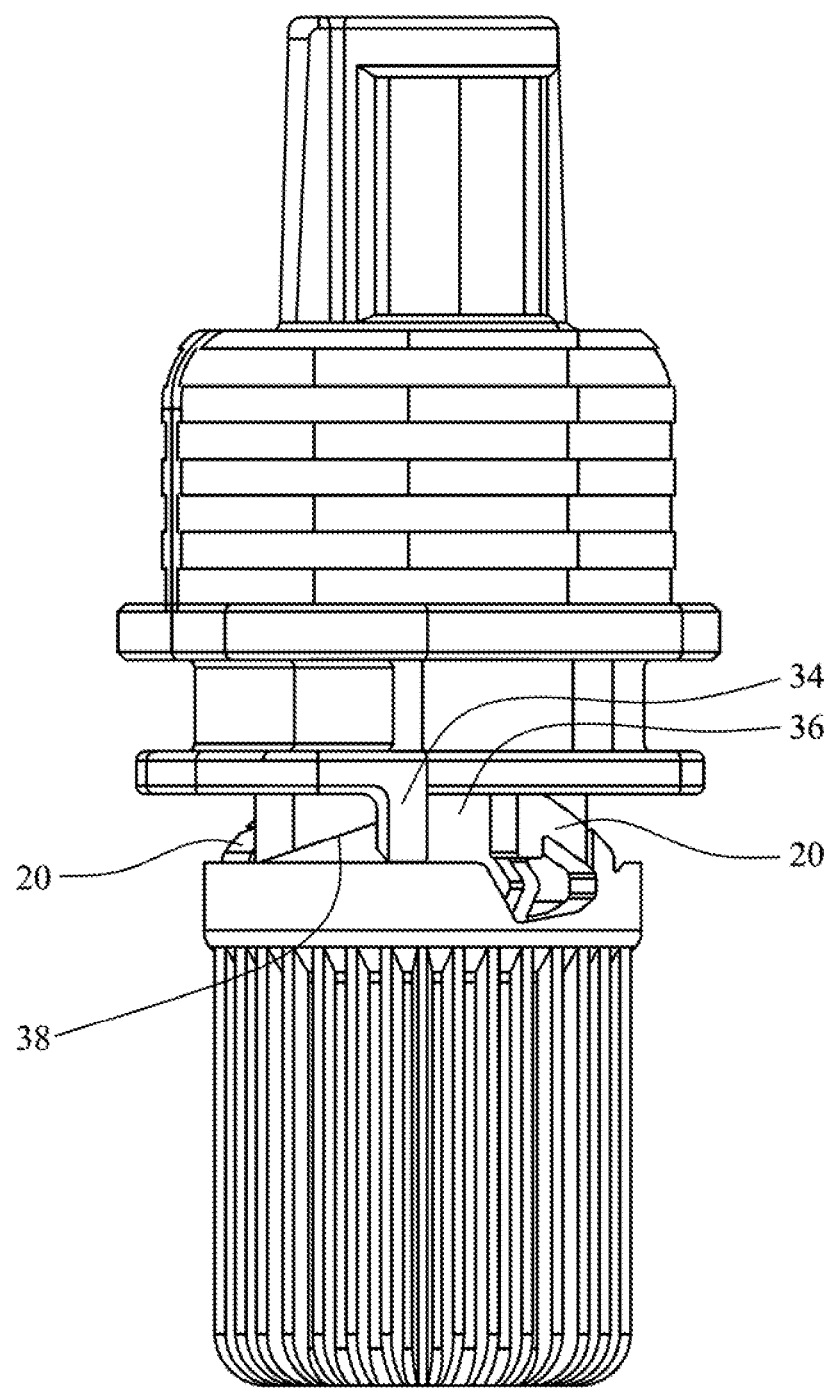
FIG. 7B: Is a front view of the tamper evident cap of FIG. 7A showing the tamper evident cap fully screwed onto the connector.

Referring now to FIG. 7A and FIG. 7B, a second functional interaction between the cap and the spout is described.

In the exemplary construction, the proximal end of the cap also includes a rotational stop feature which prevents the cap from being overtightened as it is screwed onto the spout. The rotational stop feature is in the form of a fin 38 having a stop surface 40. When stop surface 40 is brought into engagement with a radial abutment surface 42 provided on the cam 34 the cap is prevented from being screwed further onto the spout.

FIG. 7A and FIG. 7B illustrate a process of screwing and unscrewing the cap and demonstrates the independent functional interactions of the anti-tamper feature and the anti-rotational feature provided on the proximal end of the cap with the same deflecting element on the spout.

FIG. 7A shows the cap being screwed onto the spout in a clockwise direction. As the cap 14 is screwed onto the spout 12, a proximal/upper surface of the deflectable arm 20 comes into contact with the projection/cam 34. The projection 34 can slide along the sloped proximal/upper surface of the deflectable arm 20, causing the deflectable arm 20 to momentarily deflect longitudinally to allow continued longitudinal movement of the cap 14 onto the spout 12. When the projection 34 reaches and moves beyond the second end 26 of the deflectable arm 20, the deflectable arm 20 is no longer restrained by the projection 34 and therefore returns i.e. "snaps back" to its initial longitudinal position, as shown in FIG. 7A.

FIG. 7B shows the cap in the optimal position for the functionality of deflectable arm 20 (i.e., the anti-tamper feature). The stop surface 40 of fin 38 (i.e. the anti-rotational stop feature) abuts the radial abutment surface 42 of cam 34. This interaction prevents the cap from being screwed on any tighter. The cap is in a locked position. The anti-rotational stop feature blocks rotation in the clockwise direction. The anti-tamper feature blocks rotation in the anti-clockwise direction.

Figure 8:
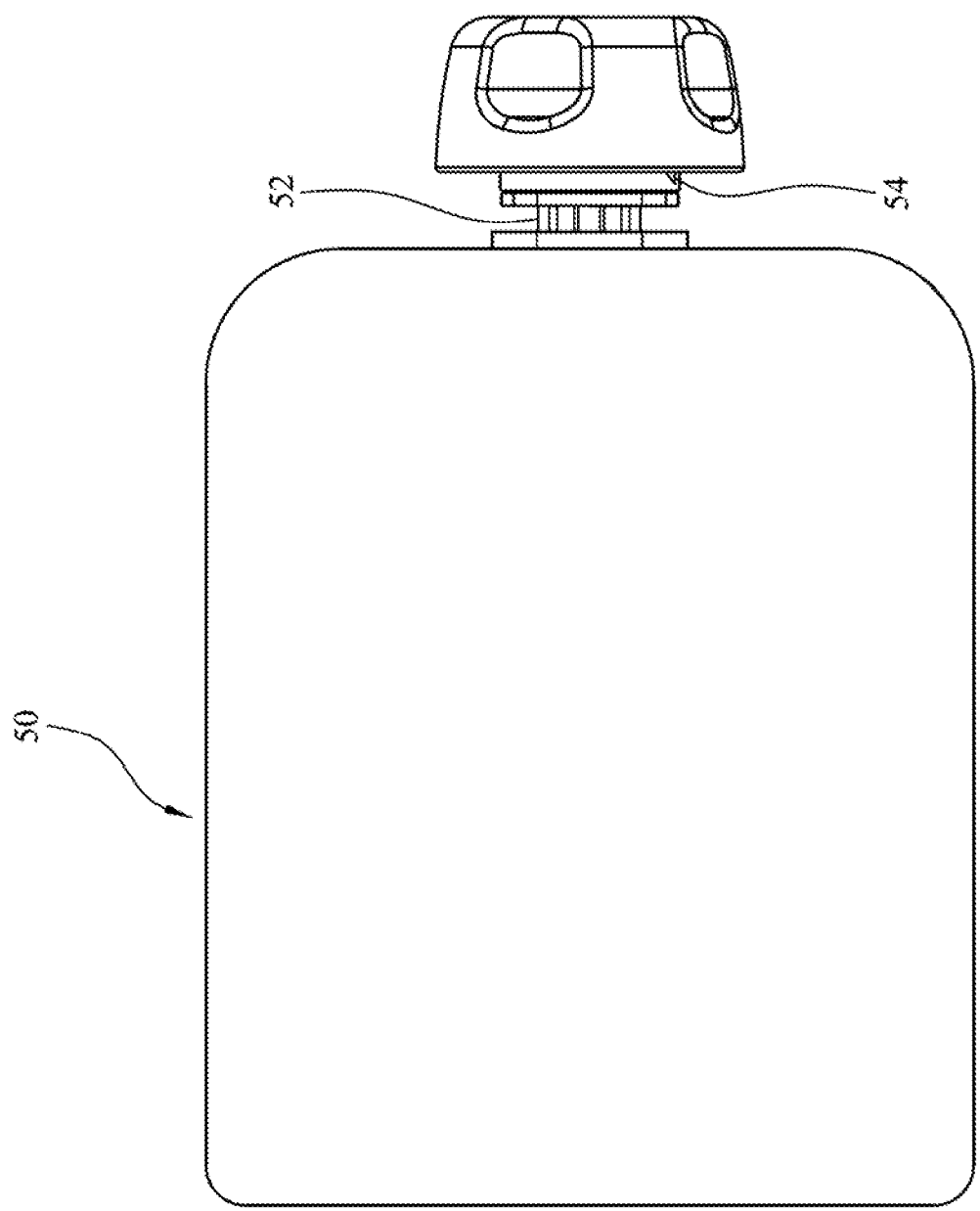
FIG. 8: Illustrates a schematic of an enteral feeding bag having an integrated ENFit connector in combination with a tamper evident cap according to a second embodiment.

Referring now to FIG. 8, an enteral feeding bag 50 according to an alternative embodiment is shown. The enteral feeding bag 50 includes an integrated female ENFit connector in the form of a spout 52. The spout 52 can be directly connected to a male ENFit connector on the end of an enteral feeding tube without the need for an adapter. A tamper evident cap 54 is screwed onto the spout 52.

Figure 9:
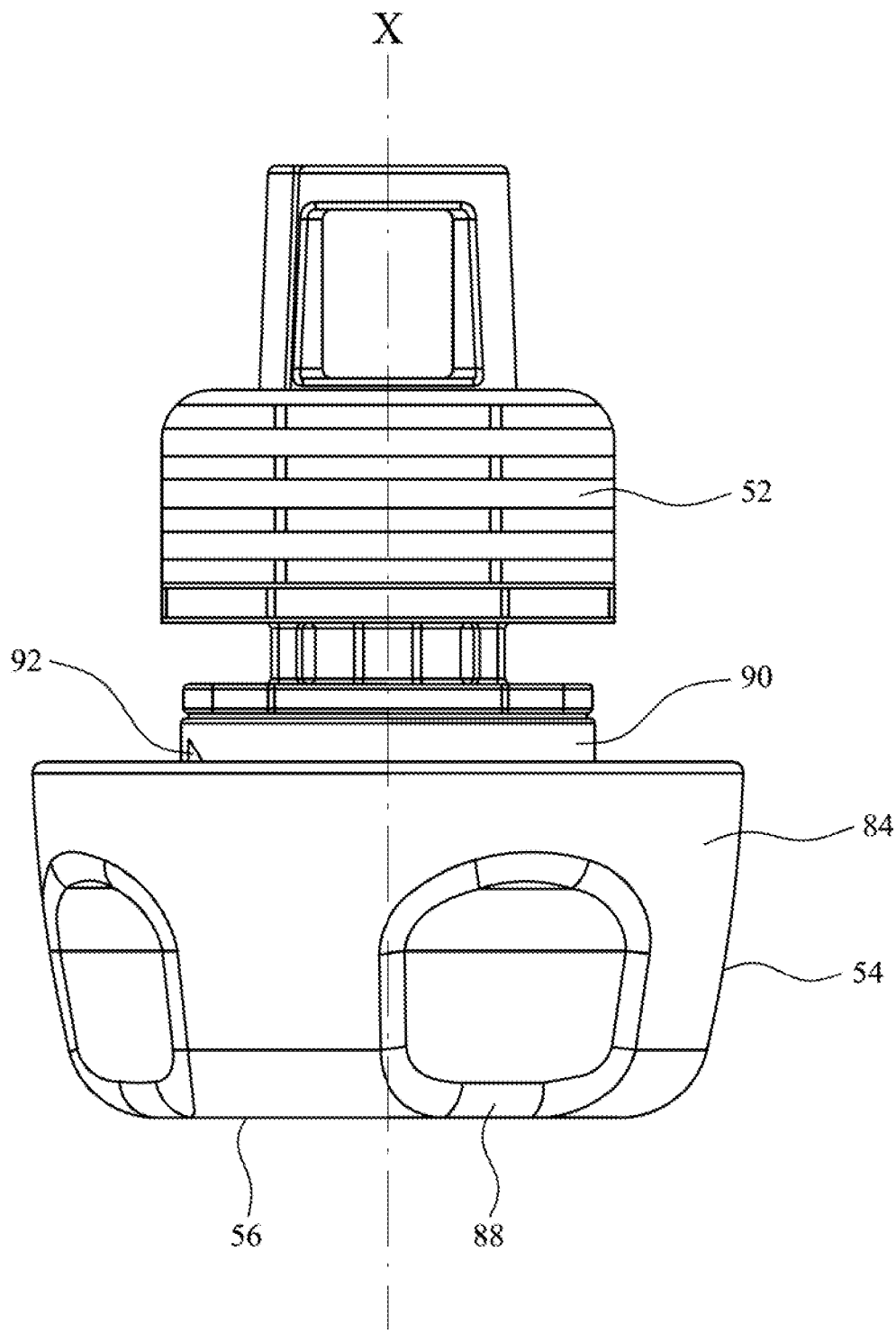
FIG. 9: is a front view of the ENFit connector and tamper evident cap of FIG. 8.
Figure 10:
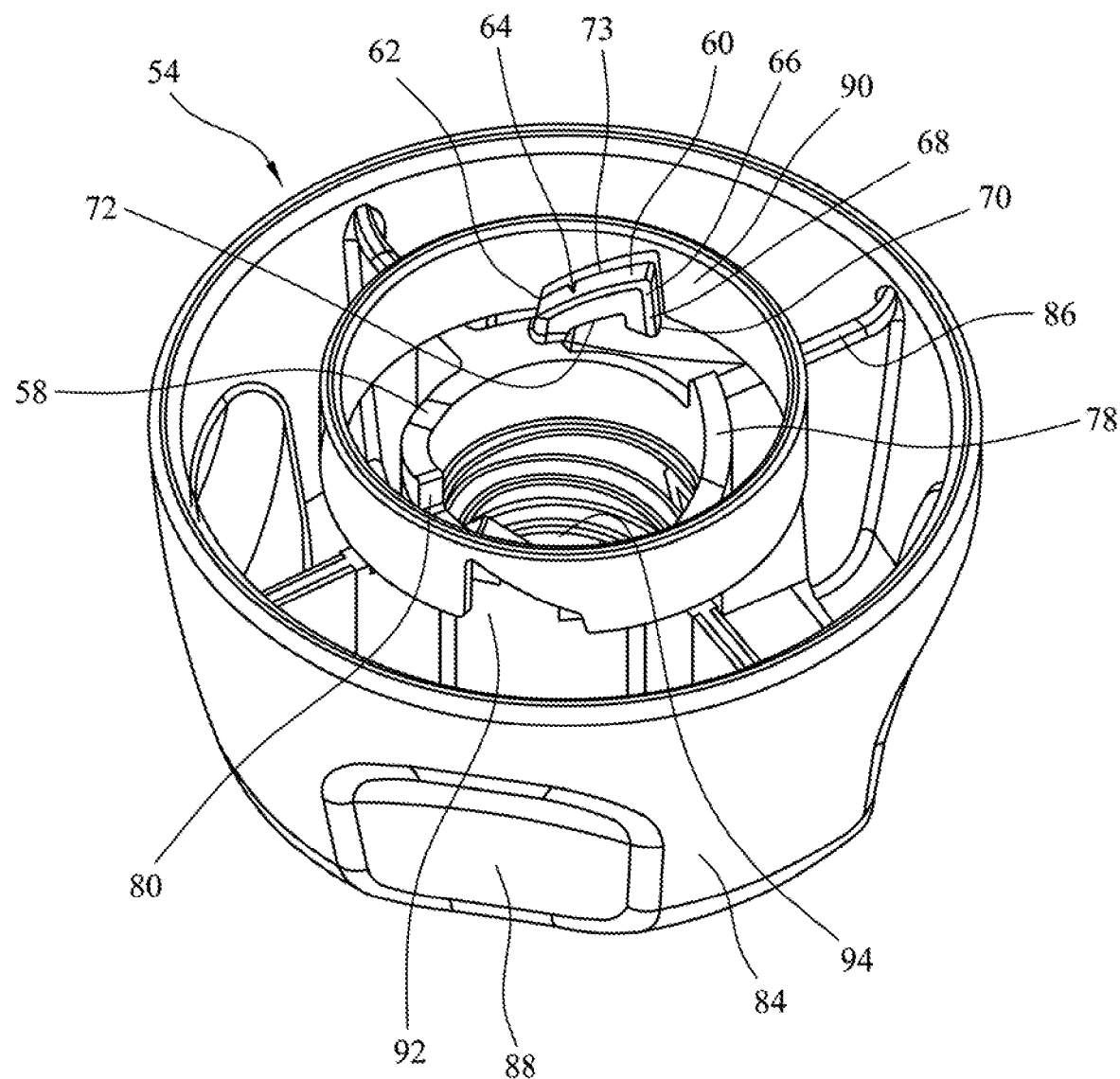
FIG. 10: is a perspective view of the tamper evident cap of FIG. 8 in an untampered state.

As best illustrated by FIGS. 9 and 10, the tamper evident cap 54 is similar to the tamper evident cap 14 but has several additional features. The cap 54 includes a male ENFit connector in the form of screw threads 94 provided on the interior surface of the cap. The threads 94 form a threaded connection with complementary screw threads 96 (shown in FIG. 11) of the female ENFit connector arranged on the spout 52. The cap 54 has a main body with a distal end 56 and a proximal end 58 and a longitudinal axis X extending therebetween. In this particular embodiment there are several features which extend beyond the proximal end 58 of the main body.

The proximal end 58 includes a tamper evident feature in the form of a deflectable arm 60. Only one deflectable arm 60 is fully visible in FIG. 10, however a second deflectable arm 60 is positioned radially opposite.

The deflectable arm 60 extends circumferentially about a portion of the main body. A first end 62 is connected to the proximal end 58 of the main body. The deflectable arm 60 is provided with a hinge 64 adjacent to the first end 62. The hinge 64 is a substantially longitudinal groove (with respect to longitudinal axis X) on a radially outwardly oriented face of the deflectable arm 60. The hinge 64 introduces a weak point in the deflectable arm 60 about which the deflectable arm 60 can deflect outwardly.

A second end 66 of the deflectable arm 60 is located more proximally than the first end 62. An acute angle is defined between the distal/lower surface 72 of the deflectable arm and the proximal end 58. The deflectable arm 60 extends circumferentially around the proximal end 58 of the cap 54, with a slope between the first and second ends 62, 66. At the second end 66 is an abutment block 68 which protrudes longitudinally towards the proximal end 58 and has a contact face 70. In this particular embodiment there is no direct connection (c.f. the snappable finger 28 of the first embodiment) between the second end 66 of the arm 60 and the proximal end 58 of the cap.

The cap 54 additionally has an external shell 84. The external shell 84 is mounted annularly around and spaced apart from the main body of the cap 54 by means of buttresses 86. In this particular embodiment there are four radially spaced buttresses 86. The external shell 84 increases the overall size of the cap 54. This reduces the risk of the cap posing a choking hazard if (for example) it is inadvertently left out after use and is picked up by a child or a patient. The external shell 84 also acts to protect the anti-tamper elements (deflectable arms 60) from damage during production, sorting and fitting.

The external shell 84 is equipped with gripping features 88 on an external surface. The gripping features 88 are indentations positioned between the points where the buttresses 86 are joined to the shell 84 and allow a user to more easily grip and twist the cap 54.

The cap 54 also has a protective ring 90 positioned annularly around the proximal end 58 of the main body. The protective ring 90 extends proximally from the proximal end 58 and in this particular embodiment is mounted on the buttresses 86. The protective ring 90 provides extra protection for the tamper evident feature (deflectable arm 60) during production and assembly. This reduces the risk of premature damage to the deflectable arms. The protective ring 90 also provides a rigid feature to aid in automated orientation and sorting of caps 54 during filling and assembly of the enteral feeding bag 50.

The protective ring 90 has an opening 92 positioned adjacent to and of a similar size and shape to the deflectable arm 60. The opening 92 allows a user to see the deflectable arm 60 when the cap is in position on the spout 52. The opening 92 also provides space for the deflectable arm 60 to deflect outwardly from an untampered state to a tampered state when the cap is twisted during removal. A user can clearly see the state of the deflectable arm 60 through the opening 92 and can thus determine whether it is in an untampered or tampered state. In this particular embodiment there are two radially opposed openings 92 corresponding to the two radially opposed deflectable arms 60.

Figure 11:
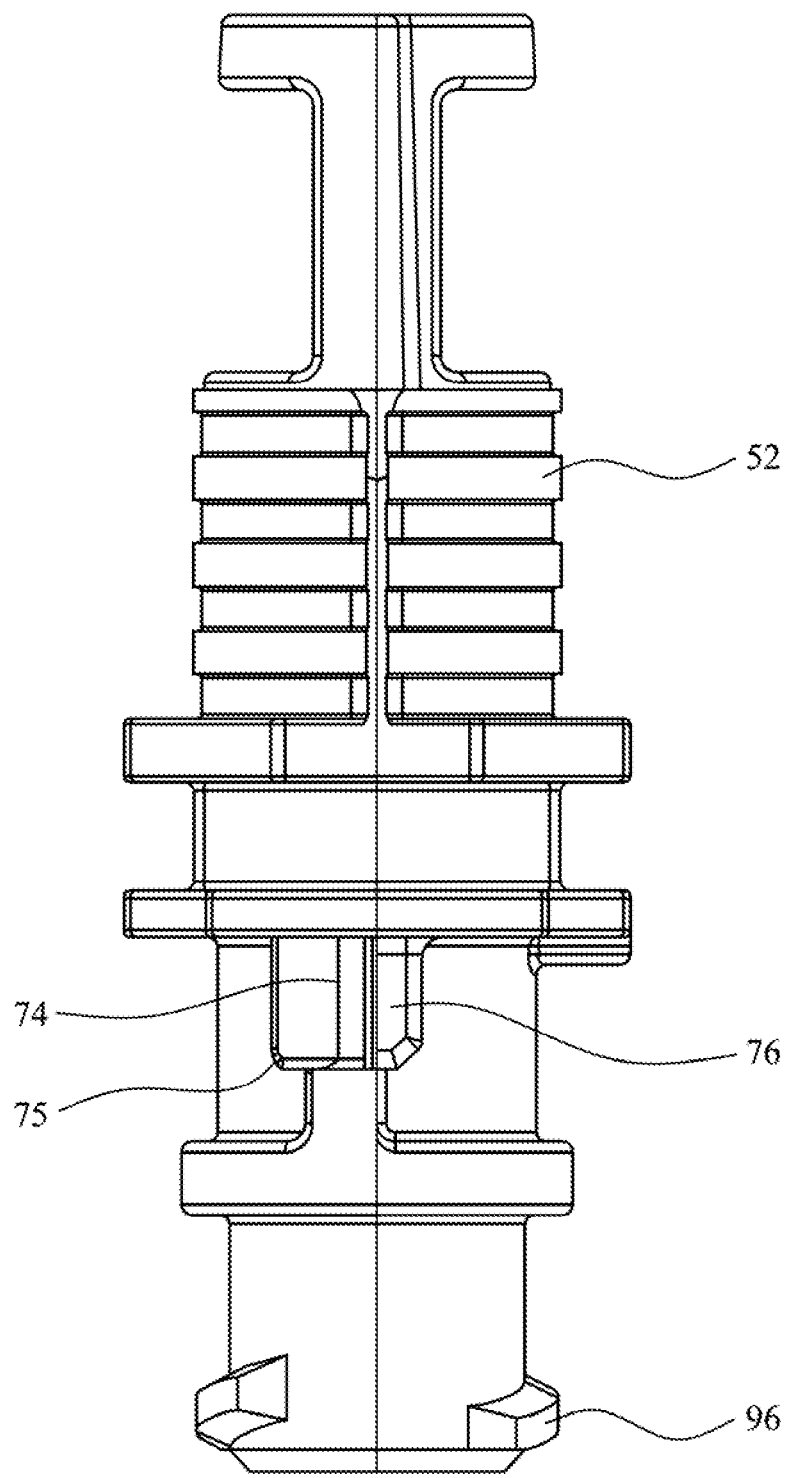
FIG. 11: is a side view of the ENFit connector of FIG. 8.
Figure 12:
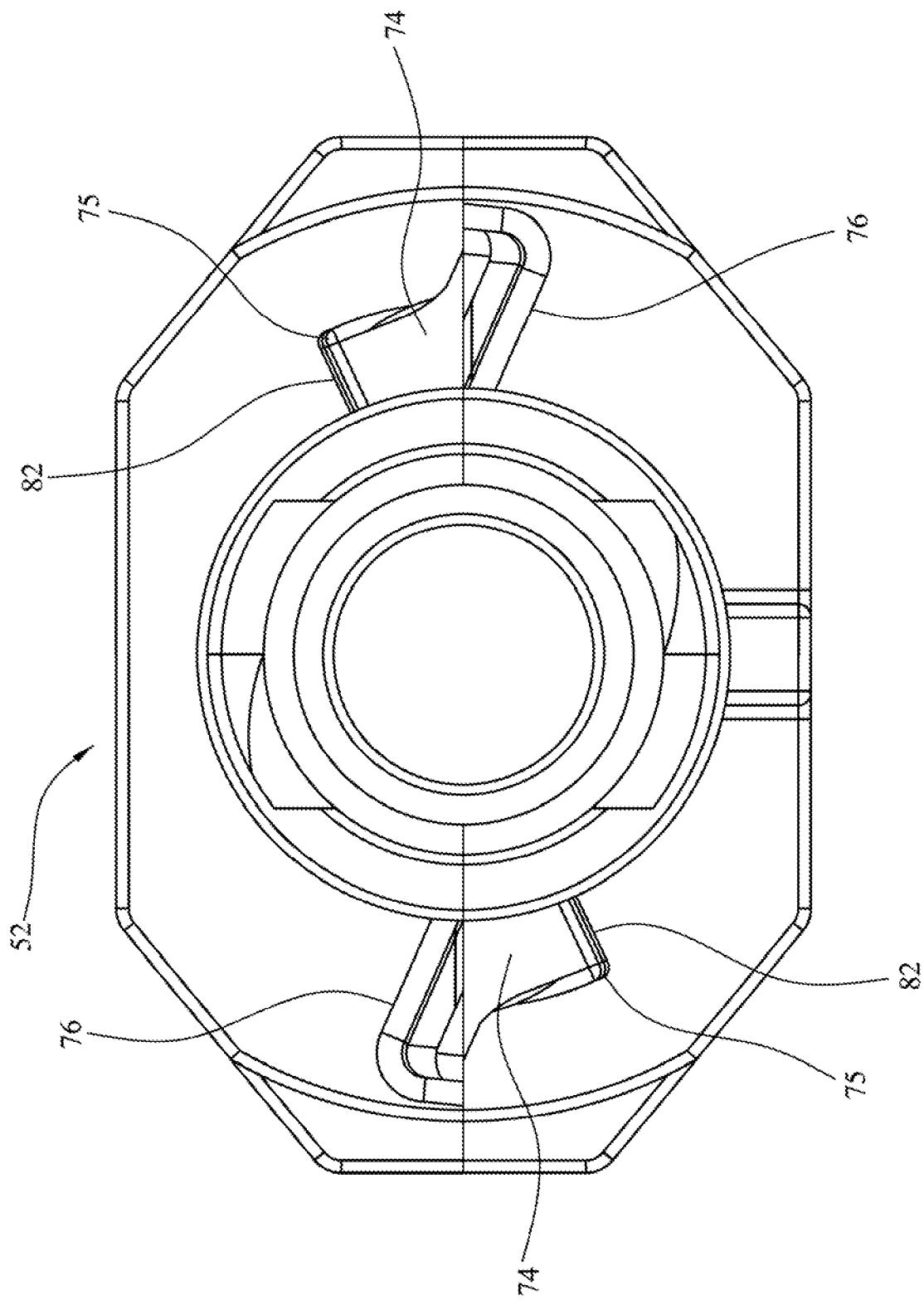
FIG. 12: is a plan view of the projections provided on the ENFit connector of FIG. 8.

Referring now to FIGS. 11 and 12, the spout 52 includes a projection 74. In this particular embodiment, there are two radially opposed projections 74 which correspond to the two radially opposed deflectable arms 60 on the cap 54. Each projection 74 is configured to interact with one of the pair of deflectable arms 60. Each projection has a first contact edge 75, a cammed surface 76, and a radial abutment surface 82. In this particular embodiment, the cammed surface 76 is substantially flat rather than concave but is angled to direct the deflectable arm 60 radially outwardly.

With reference again to FIG. 10, the proximal end 58 of the cap 54 also includes a rotational stop feature in the form of a fin 78 and a stop surface 80. In this particular embodiment there are two radially opposed rotational stop features corresponding to the two radially opposed projections 74 on the spout 52. The rotational stop features prevent the cap 54 from being over-tightened as it is screwed onto the spout, which could lead to premature damage to the tamper evident features (deflectable arms 60).

During initial assembly of the enteral feeding bag 50, the cap 54 is screwed in a clockwise direction onto the spout 52 by means of screw threads 94 and 96 on the cap 54 and spout 52 respectively. This normally occurs after the enteral feeding bag 50 has been filled. As the cap 54 is screwed onto the spout 52, a proximal/upper surface 73 of the deflectable arm 60 comes into contact with the first contact edge 75 of the projection 74. The first contact edge 75 can slide along the sloped proximal/upper surface 73, with the deflectable arm 60 deflecting longitudinally to allow continued longitudinal movement of the cap 54 onto the spout 52. When the first contact edge 75 reaches and moves beyond the second end 66 of the deflectable arm 60, the deflectable arm 60 is no longer restrained by the projection 74 and therefore returns i.e. "snaps back" to its initial longitudinal position.

As the cap 54 continues to be screwed onto the spout 52, the radial abutment surface 82 on the projection will come into contact with the stop surface 80. This prevents any further tightening of the cap 54. The cap 54 is then in an assembled, untampered state on the spout 52.

Figure 14A:
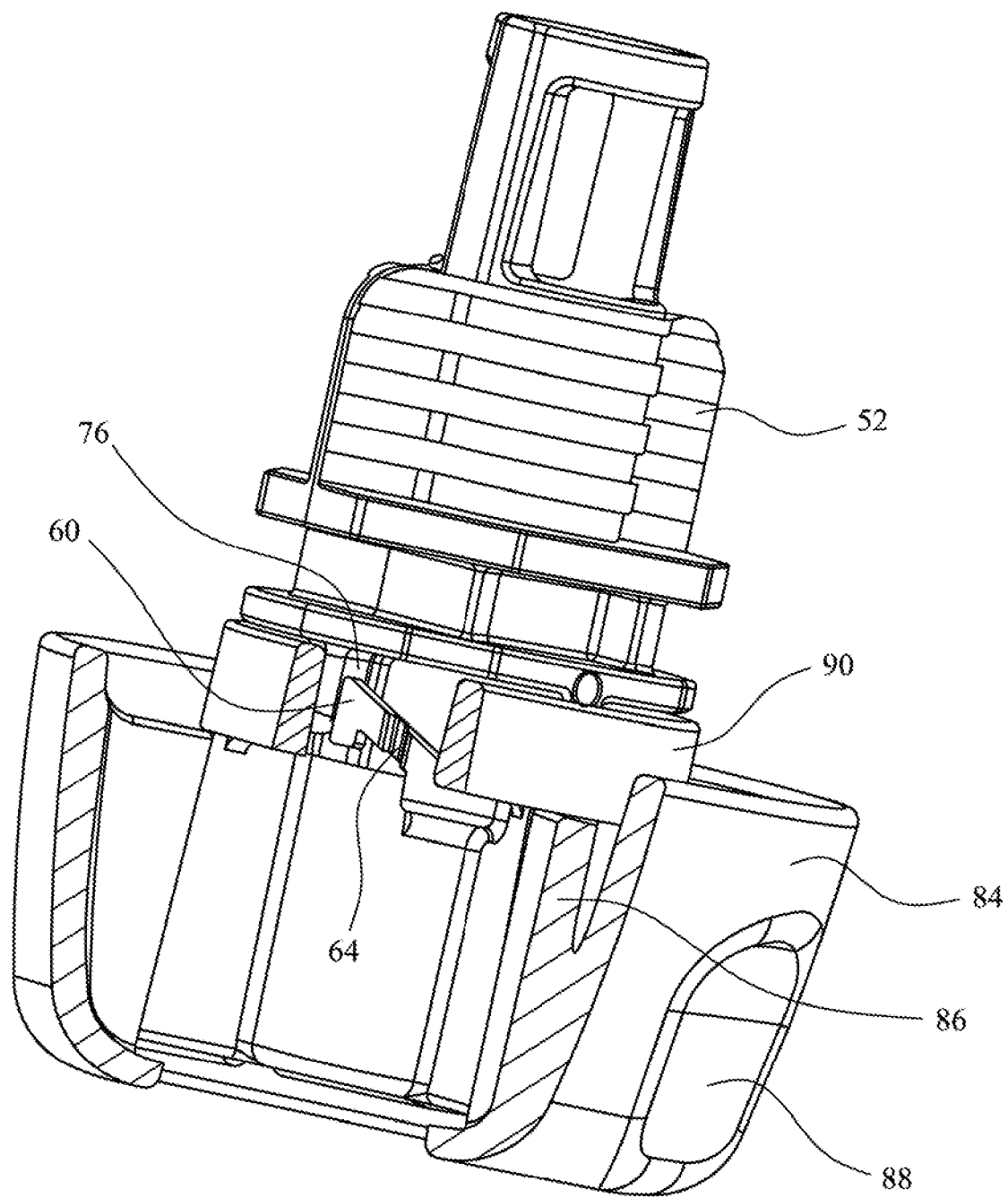
FIG. 14A: is a partial cutaway perspective view of the ENFit connector and tamper evident cap of FIG. 8 showing the tamper evident feature in an untampered state.
Figure 14B:
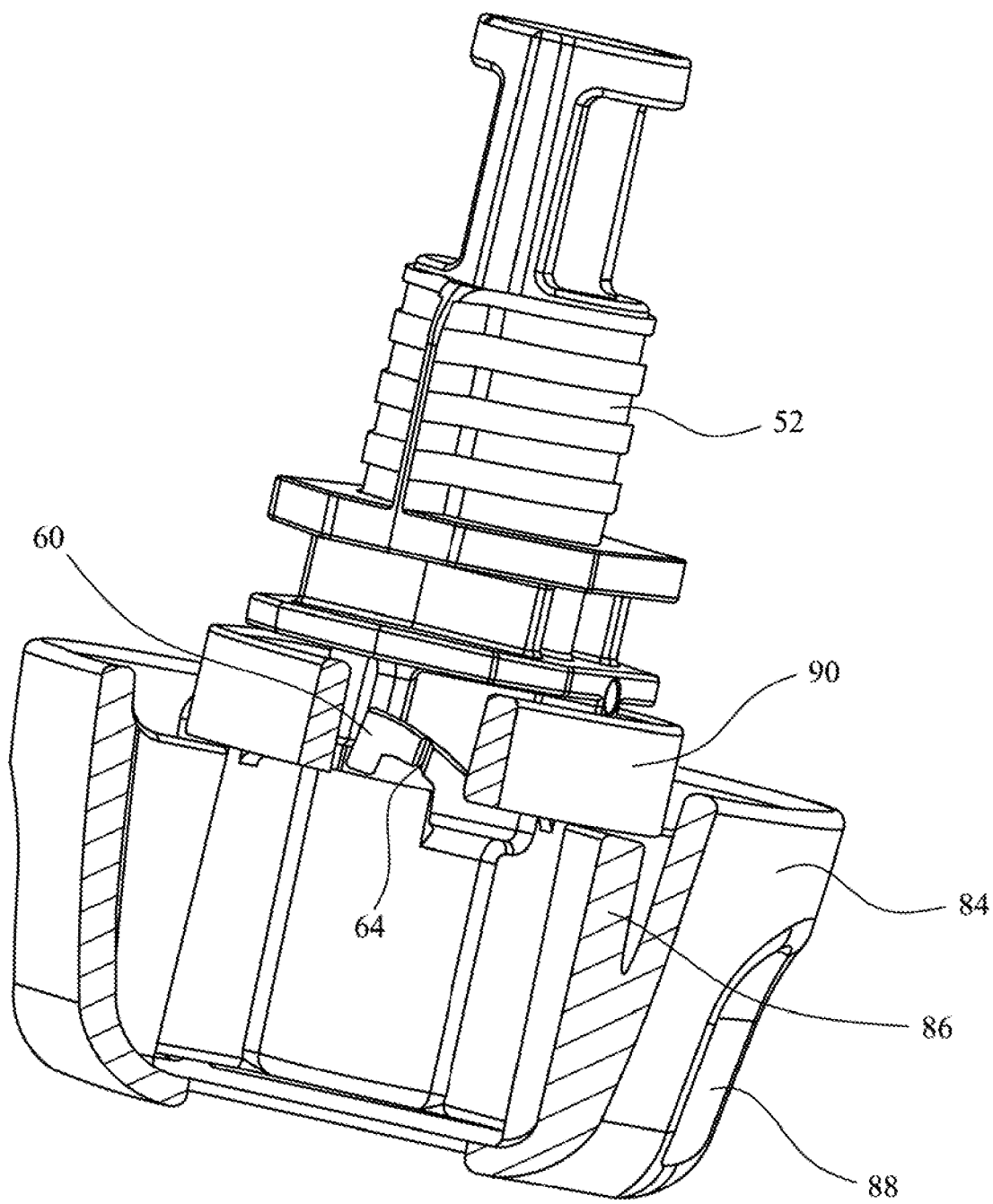
FIG. 14B: is a partial cutaway perspective view of the ENFit connector and tamper evident cap of FIG. 8 showing the tamper evident feature in an intermediate state between untampered and tampered states.

When a first user (either authorized or unauthorized) wishes to remove the cap 54 to access the contents of the enteral feeding bag 50, they can grip the external shell 84 (using the gripping features 88) and twist the cap 54 in an anti-clockwise direction. This brings the abutment block 68 at the second end 66 of the deflectable arm 60 into contact with the cammed surface 76 of the projection 74, as best illustrated in FIG. 14A. The deflectable arm 60 cannot move passed the projection 74 without deflecting. The shape of the cammed surface 76 together with the hinge 64 causes the second end 66 of the deflectable arm 60 to deflect radially outward in preference to deflecting radially inward or longitudinally, as shown in FIG. 14B. This deflection is therefore in a different plane to the momentary longitudinal deflection of the arm 60 as the cap 54 is screwed onto the spout 52.

Figure 14C:
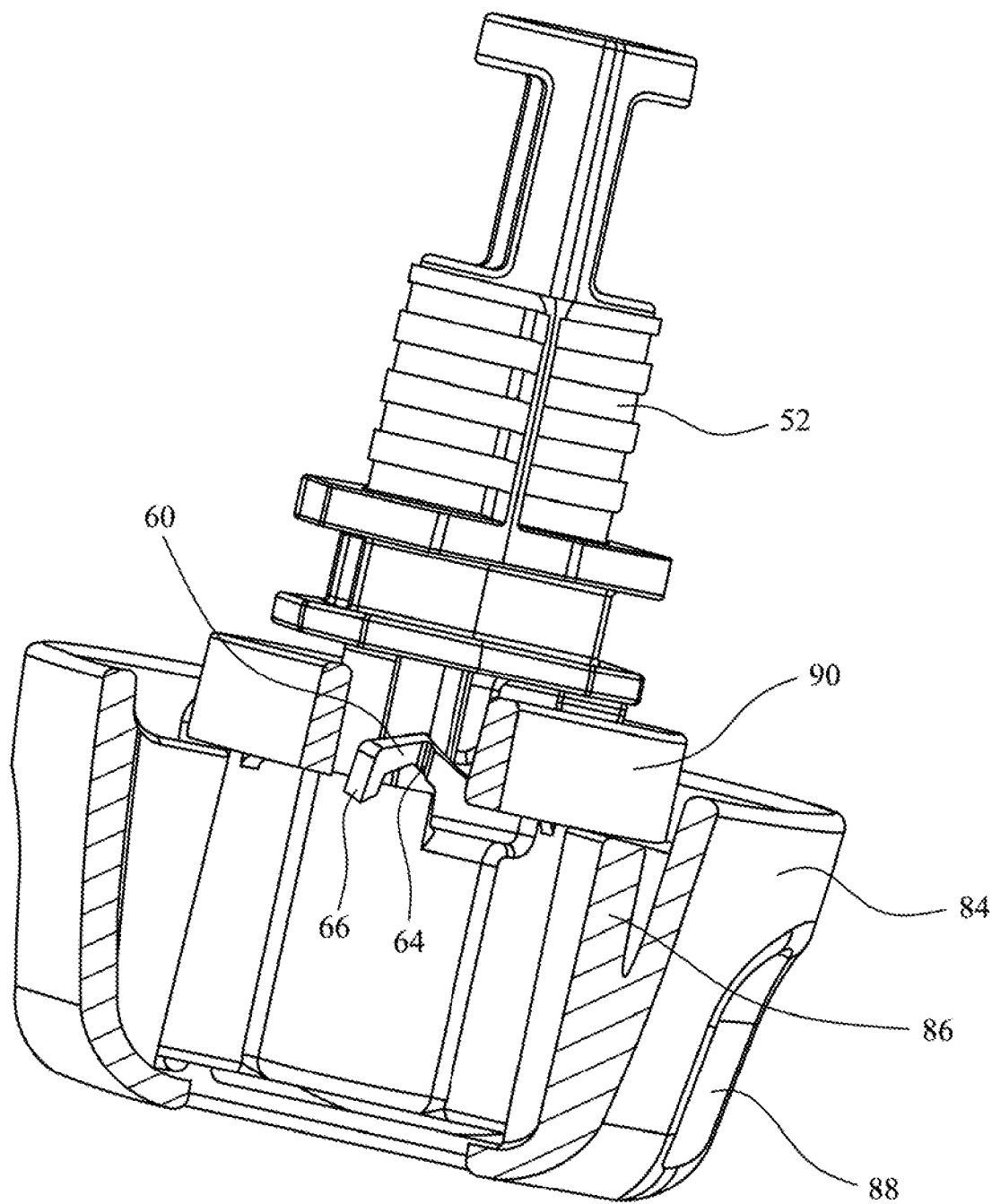
FIG. 14C: is a partial cutaway perspective view of the ENFit connector and tamper evident cap of FIG. 8 showing the tamper evident feature in a tampered state.

The outward radial deflection of the deflectable arm 60 is facilitated by the hinge 64 which provides a weak point on the radially outer surface of the deflectable arm 60, thus facilitating outward movement. Unlike the longitudinal deflection during assembly where the deflectable arm 60 returns to its initial position after deflection, the weak point at the hinge 64 causes the arm to deflect permanently outwards as the cap is unscrewed. The deflectable arm 60 may shear off completely at or about the hinge 64 or may remain attached but permanently deformed, as shown in FIG. 14C. When the deflectable arm 60 deflects outwardly in this manner there will be an audible "click" and haptic feedback to the user through their hand gripping the cap 54.

Figure 13:
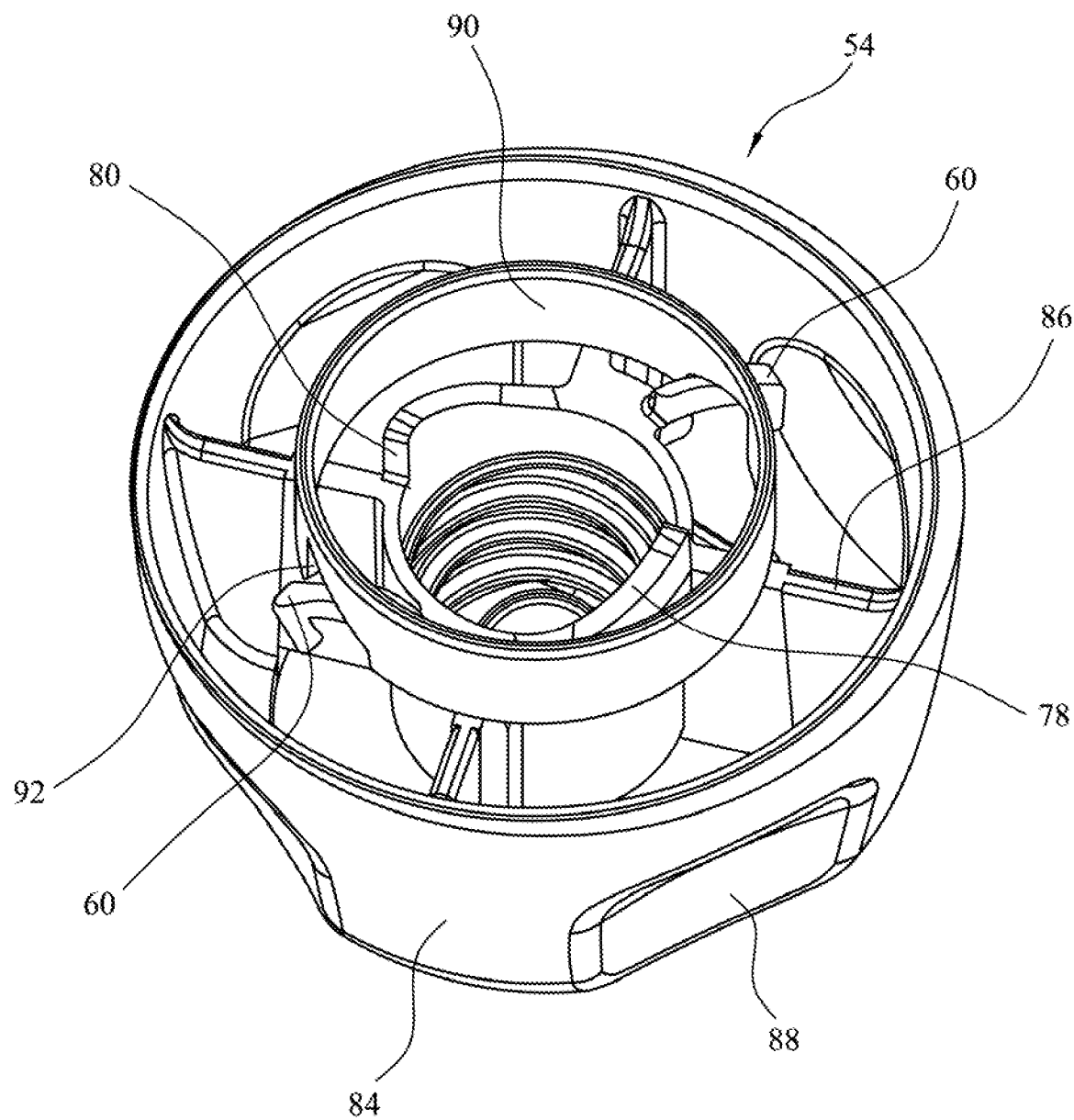
FIG. 13: is a perspective view of the tamper evident cap of FIG. 8 in a tampered state.

After the cap 54 has been removed from the spout 52 once, the deflectable arms 60 will be permanently deformed outwardly in a tampered state, as shown in FIG. 13 and FIG. 14C. The tampered state of the deflectable arms 60 can be clearly visualized by a user through the openings 92 on the protective ring 90.

The deflectable arms 60 remain visible through the openings 92 when the cap 54 is screwed onto the spout 52. Thus a user can clearly identify whether a cap 54 has previously been unscrewed even if it has subsequently been screwed back onto the spout 52. Furthermore, when a cap 54 which has already been unscrewed is unscrewed again (for example by a second user) then the user will not hear an audible "click" or receive haptic feedback, as the deflectable arms 60 will already be permanently deformed. The deflectable arms 60 therefore provide a threefold indication (visual, audible, haptic) of prior tampering.

Although particular constructions of the invention have been described, it will be appreciated that many modifications/additions and/or substitutions may be made within the scope of the claimed invention.

The invention claimed is:

1. A tamper evident cap for screwing onto a fluid outlet provided on an enteral fluid source, the cap comprising:
    an elongate main body having a distal end and a proximal end and a longitudinal axis extending therebetween;
    a tamper evident feature comprising a deflectable element, wherein the deflectable element is configured to be momentarily deflectable in the longitudinal direction by a deflecting element provided on the fluid outlet, wherein the deflecting element contacts and applies force in a longitudinal direction to the deflectable element to momentarily deflect the deflectable element as the cap is screwed onto the fluid outlet, and wherein the deflectable element is configured to be permanently deflected outwardly in relation to the longitudinal axis by the deflecting element provided on the fluid outlet as the cap is unscrewed from the fluid outlet to provide a visual indication that the cap has been unscrewed.

2. The tamper evident cap of claim 1, wherein the tamper evident feature comprises a plurality of deflectable elements spaced apart about a proximal end of the cap.

3. The tamper evident cap of claim 2, wherein a first deflectable element and a second deflectable element are radially opposed on the proximal end of the cap.

4. The tamper evident cap of claim 1, wherein the or each of the first and second deflectable elements is a deflectable arm.

5. The tamper evident cap of claim 1, wherein the cap further includes a rotational stop feature to prevent overtightening of the cap as the cap is screwed onto the fluid outlet.

6. A kit comprising a tamper evident cap according to claim 1, and an enteral fluid source.

7. An enteral feeding bag comprising:
    a fluid outlet comprising a connection portion configured to form a connection with an end of an enteral feed tube, and
    a tamper-evident cap according to claim 1 removably attached to the fluid outlet.

8. The enteral feeding bag of claim 7, wherein the fluid outlet comprises a projection extending outwardly from a wall of the fluid outlet, wherein the projection is configured to momentarily deflect the or each deflectable element in a longitudinal direction as the cap is screwed onto the fluid outlet, and to permanently deflect the or each deflectable element as the cap is unscrewed from the fluid outlet.

9. The enteral feeding bag of claim 8, wherein projection is a cam.

10. The enteral feeding bag of claim 9, wherein the cam has a cammed surface that is generally concave.

11. The enteral feeding bag of claim 7, wherein the connection portion on the fluid outlet is a connector which complies with the requirements of International Standard ISO 80369-3.

* * * * *